United States Patent [19]

Rubin

[11] 4,358,586

[45] Nov. 9, 1982

[54] DETECTION AND ISOLATION OF ENDORPHIN MRNA USING A SYNTHETIC OLIGODEOXYNUCLEOTIDE

[76] Inventor: Harvey Rubin, 2560 First Ave., San Diego, Calif. 92103

[21] Appl. No.: 219,435

[22] Filed: Dec. 23, 1980

[51] Int. Cl.$^3$ .................... C07H 21/04; C12N 15/00
[52] U.S. Cl. .................................... 536/27; 536/29; 536/30; 435/172
[58] Field of Search ............................ 536/27, 28, 29; 435/172

[56] References Cited

PUBLICATIONS

Roberts, J., et al., Proc. Natl. Acad. Sci., vol. 76, pp. 2153–2157, 1979.
Chemical Abstracts, vol. 91, p. 419, Abstract No. 53491w, 1979.

Primary Examiner—Blondel Hazel
Attorney, Agent, or Firm—Frank D. Gilliam

[57] ABSTRACT

A synthetic oligodeoxynucleotide complementary to endorphin mRNA and a method of using it to detect and isolate endorphin mRNA and cDNA from human and rabbit pancreas. A unique 15 base oligodeoxynucleotide dCATGAACCCGCCGTA wherein T represents thymine, G represents guanine, A represents adenine, and C represents cytosine and where at least 13 of the 15 nucleotides are as indicated (one of those indicated may be instead one of the other three mentioned nucleotides) has been found to be complementary to endorphin mRNA. To isolate endorphin mRNA, total RNA is first extracted from human brain and A+ is isolated from the total RNA. Other tissues may be used. The A+ RNA is then treated with the oligodeoxynucleotide, and the resulting hybridized RNA is enzymatically converted to endorphin mRNA:cDNA which can then be purified and used in a conventional manner to produce endorphin by cloning techniques.

2 Claims, No Drawings

DETECTION AND ISOLATION OF ENDORPHIN MRNA USING A SYNTHETIC OLIGODEOXYNUCLEOTIDE

BACKGROUND OF THE INVENTION

This invention relates in general to the isolation of specific ribonucleic acid molecules and, more specifically, to the detection and isolation of endorphin mRNA.

Recently, considerable research effort has been expended in investigating the intricate relationship between genes and proteins. A wide variety of deoxyribonucleic acid (DNA) and ribonucleic acid (RNA) molecules have been detected and have been found to perform a variety of biochemical functions. Some ribonucleic acid polymers have been found to serve a "messenger" function, providing a template guiding definite sequences of amino acids in the assembly of proteins. These messenger RNA (or mRNA) molecules, if detected and isolated, can be used to "manufacture" DNA molecules having the capability of producing selected useful amino acid sequences, such as insulin.

Endorphin is polypeptide hormone produced by cells in the pituitary gland, brain, gut and in the alpha cells of the Islets of Langerhans. It has been called "natural morphine." Small amounts have been isolated, appearing to be part of a much larger straight chain polypeptide. Endorphin has been found to be useful in producing a slowed movement of the gut, relaxing smooth muscle and preventing pain.

Enkephalin may have the sequence: Tyrosine-Glycine-Glycine-Phenylalanine-Leucine ("Leu-enkephalin") or Tyrosine-Glycine-Glycine-Phenylalanine-Methionine ("Met-enkephalin"). Mixtures of these forms, which have quite similar properties, are generally simply referred to as enkephalin.

While the enkephalin five amino acid sequence may exist alone, it is most effective when incorporated into the longer (31 amino acid) endorphin sequence. However, no satisfactory method exists in the prior art for the detection or isolation or reasonable quantities of the several types of endorphin mRNA. Thus, there is a continuing need for an improved method for isolating and purifying endorphin mRNA.

SUMMARY OF THE INVENTION

The above problems have been overcome by my method of isolating endorphin mRNA from a suitable source, such as a human brain using a unique 15 base oligodeoxynucleotide. A short segment of the endorphin amino acid sequence is used to deduce the sequence of a unique oligodeoxynucleotide complementary to the endorphin mRNA. This oligodeoxynucleotide is then used as a sensitive and specific probe for the endorphin mRNA.

Basically, my method consists of the steps of isolation of pancreas, human brain or adrenal gland A+ RNA, hybridization with the specific selected oligodeoxynucleotide and enzymatic synthesis of endorphin copy DNA which is subsequently isolated in pure form. This endorphin cDNA can then be used in a conventional manner to produce endorphin by recombinant techniques.

DETAILED DESCRIPTION OF THE INVENTION

I have found that certain 15 unit oligodeoxynucleotides may by synthesized which complement the segment of endorphin mRNA coding for specific sequences of the amino acids. These 15-mers will rapidly and specifically hybridize pancreas endorphin A+ RNA (poly A containing mRNA). These 15-mers are specific and sensitive probes for endorphin mRNA sequences in heterogeneous populations of RNA (ribonucleic acid).

The enkephalin sequence (Tyr-Gly-Gly-Phe-Leu or Tyr-Gly-Gly-Phe-Met) may occur as a discrete entity, but ordinarily is captured as part of a longer sequence. Typical of these are endorphin, a 31 amino acid sequence, or dynorphin, a 13 amino acid sequence, each including the enkephelin 5 amino acid sequence. I have found that optimum stability is obtained with the endorphin sequence. Other chain lengths may be preferred for other desired characteristics.

The 15-mer used may be any suitable variation in my novel 15 base oligonucleotide. Best results have been obtained with the 15 base oligonucleotide dCATGAACCCGCCGTA, which is therefore preferred for use in my purposes. Other typical sequences which have been found to produce useful results have the general formula CATxAAyCCyCCGTA, wherein "A" represents adenine, "T" represents thymine, "G" represents guanine, "C" represents cytonine, "x" represents guanine or adenine and "y" represents guanine, thymine, cytosine or adenine. Excellent results are obtained so long as at least 13 of the 15 nucleotides are as shown in the preferred arrangement.

My preferred method for the isolation of endorphin mRNA sequences involves the chemical synthesis of a complementary oligonucleotide deduced from favorable short sequences of amino acids, preferably the sequence detailed above. The oligodeoxynucleotide dCATGAACCCGCCGTA may be prepared in any suitable manner. Typical is the phosphodiester method described by Agarwal et al.(1972) Angewandte Chem. Int. Ed. Eng. 11, 451. Its nucleotide sequence is confirmed by the method of Tu, C.P.D. et al. Anal. Biochem., 74: 73–93 (1976).

My first step is the isolation of A+ RNA from fresh tissue samples. Samples of pancreas, pituitary or adrenal glands or brain are obtained from autopsy samples. While any suitable starting material such as brain, adrenal, pancreas and pituitary tissue may be used, human brain and adrenal gland tissue is preferred. Total RNA is obtained by the guanidine hydrochloric acid extraction procedure using glassware which had been previously baked and treated with diethylpyrocarbonate to remove any traces of RNase. This type of technique is described by R. A. Cox, Meth. Enzymol. 12B:120–129 (1968). A+ RNA is isolated on oligo-dT-cellulose obtained from Collaborative Research, using the technique described by J. A. Bantle et al., in Anal. Biochem. 70:413 (1976). All fractions of RNA are assayed for purity and intactness by electrophoresis in 1.5% agarose gels in the presence of 4 mM $CH_3HgOH$ by the method described by J. M. Bailey et al., in Anal. Biochem. 70:75 (1976), and for translatability in the wheat embryo in vitro system described by A. Marcus et al., in Methods in Enzymeology 30, 479 (1974). In vitro translation products are monitored on sodium dodecyl sulfate/9% polyacrylamide gels as described by U. K. Laemmli, Nature 227:680 (1970). The RNA preparations used here in general stimulate the incorporation of $^{35}$S-methionine into large protein products 3 to 5 fold over background.

The radiolabeled 15 mer is then hybridized. Hybridization reactions are carried out at 20° C. in 0.5M sodium phosphate buffer solution (pH 6.8) containing 0.2% sodium lauryl sulfate. Solutions containing about 1 mg adrenal A+ mRNA and 15 mer ($10^6$ to $10^7$ cpm/ul) were heated to 100° C. for 1-2 minutes, then cooled to 20° C. and allowed to reanneal. The extent of reaction as a function of time is monitored on an Ultrogel A-44 column (0.7 by 100 cm) in 0.12M sodium phosphate buffer including about 0.1% sodium lauryl sulfate. The sequence excess of 15 mer to its complement in mRNA is generally 300:1. The reaction rates are expressed in terms of equivalent $C_o t$, as described by R. J. Britten, et al., Methods Enzymol. 29:363 (1974). Control reactions utilizing yeast RNA and rat liver RNA under the same conditions yield no detectable hybrids, indicating specific hybridization with endorphin RNA. Thermal denaturation profile comparisons and comparison of the kinetics of hybridization confirm that the synthetic oligodeoxynucleotide reacts specifically with endorphin mRNA sequences. Thus, a practical method of specific detection of human endorphin mRNA is provided by this invention.

While any suitable temperature may be used for the formulation of the hybrids, I have found that if the temperature is too high, there will be little or no capture, while temperatures which are too low tend to produce false captures. While temperatures in the range of from about 0° to 80° C. produce useful results, best results are obtained with temperatures in the range of from about 10° to 40° C.

I produce endorphin mRNA complementary DNA (endorphin cDNA) using the synthetic oligonucleotide as a specific probe using conventional techniques. Briefly one such conventional method involves the addition of a suitable enzyme and a mixture of thymine, guanine, cytosine and adenine (as their respective deoxynucleotide triphosphates) to extend the primer, and thus to form endorphin cDNA molecules in accordance with the endorphin messenger RNA "template"; separation of the mRNA from the endorphin cDNA such as by alkaline hydroysis to disperse the RNA, gel electrophoresis to isolate the specific endorphin cDNA, cutting out the appropriate band from the electrophoretic gel (as indicated by radioactive tagging, typically), destruction of the agarose gel with sodium perchlorate, which leaves only the desired DNA, which can then be cloned using standard techniques. Thus a practical method for the isolation of human and rabbit endorphin mRNA:cDNA is provided by this invention. Of course, the endorphin mRNA:cDNA produced by the method of my invention can be used in any other method, as desired.

The endorphin mRNA may also be isolated by the following method. The 15-mer obtained as described above is extended to 15-mer poly-C by the use of polynucleotide phosphorylase plus cytosine di-phosphate plus 15-mer by the technique described in N. Davidson, Biochemistry 17, 3883 (1978). The 15-mer is then complexed to DBM chips and A+ RNA from brain, pancreas, adrenal, medula or pituitary is hybridized to the 15-mer immobilized on the chips by the procedure described by H. Rubin, BBRC 93, 941 (1980). Hybridized mRNA endorphin on DBM chips is washed with a buffer until no further counts are eluted. The pure mRNA endorphin is isolated from the chips by heating water bath to about 100° C. for about 10 minutes, removing chips, leaving mRNA (endorphin) 95%+ pure in the buffer. To show that the species of mRNA is pure, the mRNA is run on alkaline agarose gel, the mRNA is translated in a wheat germ system, the protein products of translation are immunoprecipitated and the resulting released protein (released from anti-endorphin) on acrylamide gel is found to have the correct molecular weight, about 31,000. The mRNA (endorphin) is then added to reverse transcriptose together with dC, dG, dA and dT. Reverse transcripted cDNA (endorphin) is obtained as described in first paragraph, page five hereof. This is adaptable for cloning by state-of-the-art procedures.

The cloning techniques used to produce endorphin from endorphin mcDNA may be any commonly used procedure such as that which has been used to produce active insulin. Briefly the method involves enzymatic insertion of endorphin mcDNA into a bacterial gene carried on a larger piece of DNA called a plasmid, inclusion of the plasmid into a suitable host bacterium, and subsequent synthesis of the desired protein formed by the bacterium.

I have found that mRNA (endorphin) can also be captured by another 15-mer, which I call Type II (the above-described 15-mer being then Type I). This mRNA (endorphin) Type II may be captured by a deoxynucleotide, 15 nucleotides in length, derived from consideration of amino acids $^{27}$His$^{28}$Lys$^{29}$Lys$^{30}$Gly$^{31}$Gln in beef endorphin. The preferred oligonucleotide in this case is dCTGGCCTTTTTTGTG. Other useful sequences include CTGACCTTTTTTGTG, CTGTCCTTTTTTGTG and CTGCCCTTTTTTGTG. Tyrosine$_{27}$+glutamic acid $_{31}$ occur in human endorphin, compared to histidine$_{27}$+glutamine$_{31}$ in beef endorphin. If desired, tyrosine may be inserted for histidine in position 27 of endorphin. By a series of conventional transformations the codon of tyrosine can be inserted in place of histidine, resulting in the following probe: CTGGCCTTTTTTGTA. Similarly, if it is desired to replace glutamine by glutamic acid in position 31, I would insert a change in one nucleotide, i.e., CTCGCCTTTTTTGTG. These may be used in the methods described above to obtain a workable clone.

It is further possible to hybridize to both ends of mRNA endorphin by 15-mer probes. After pure mRNA has been isolated as described above in paragraph 2, page 5, 15-mer Type I and 15-mer Type II are hybridized to their respective ends of endorphin mRNA. By treatment with reverse transcriptose and four different deoxynucleotides, the four bases will fill the spaces in between the Type I and Type II 15-mers, along the mRNA chain. The same procedure as described above is used for working up the DNA compound. If desired, another probe could be inserted along the mRNA chain between the Type I and Type II 15-mer probes. Typically, this additional probe would hybridize to nucleotides 16-30, 17-31, 18-32, etc. After the remaining nucleotides are filled in as described earlier in this paragraph, processing to DNA and cloning can continue as described above.

Multiple hybridization permits us to produce a selected endorphin, e.g., human rather than bovine endorphine, with all 31 amino acids correct. For example, the third probe may be desirable if amino acids in positions 6-26 need to be changed from those coded for by the original mRNA (endorphin). Typically, human rather than bovine endorphin can be produced with bovine original mRNA by substituting glutaminic acid for glutamine, as in use of 15-mer oligodeoxynucleotide probes on page 6, acid at position 31 and tyrosine for histidine at position 27. Including different amino acids in selected positions may be desirable to enhance drug effect, reduce rate of destruction by proteinases, increase binding to opiate receptors, etc.

Other ramifications, applications and variations of this invention will occur to those skilled in the art upon reading this disclosure. These are intended to be included within the scope of the invention, as defined in the appended claims.

I claim:
1. As a composition of matter, a 15 base oligodeoxynucleotide having the sequence CATxAAyCCyCCGTA wherein "A" represents adenine, "T" represents thymine, "G" represents guanine, "C" represents cytosine, "x" represents guanine or adenine, and "y" represents guanine, thymine, cytosine or adenine.
2. The composition of matter according to claim 1 wherein said 15 base oligodeoxynucleotide has the sequence CATGAACCCGCCGTA.

* * * * *